United States Patent [19]
Kalvin

[11] Patent Number: 5,933,471
[45] Date of Patent: Aug. 3, 1999

[54] SYSTEM AND METHOD FOR REDUCING RECONSTRUCTION ARTIFACTS IN COMPUTED TOMOGRAPHY IMAGES

[75] Inventor: Alan David Kalvin, Irvington, N.Y.

[73] Assignee: International Business Machines Corporation, Armonk, N.Y.

[21] Appl. No.: 09/025,677

[22] Filed: Feb. 18, 1998

Related U.S. Application Data

[60] Provisional application No. 60/038,330, Feb. 26, 1997.

[51] Int. Cl.$^6$ .................................................. A61B 6/03
[52] U.S. Cl. ............................................. 378/4; 378/901
[58] Field of Search ................................... 378/4, 8, 901

[56] References Cited

U.S. PATENT DOCUMENTS 5,338,936  8/1994  Gullberg et al. .................... 250/363.04

OTHER PUBLICATIONS

Heang K. Tuy, "An Algorithm to Reduce Clip Artifacts in CT Images", SPIE vol. 1652 Medical Imaging VI: Image Processing (1992), pp. 635–643.

H. Soltanian–Zadeh et al., "CT Artifact Correction: An Image Processing Approach", SPIE Medical Imaging, Feb. 1996.

G. Wang et al., "Iterative Deblurring for CT Metal Artifact Reduction", IEEE Transactions on Medical Imaging, vol. 15, No. 5, Oct. 1996, pp. 657–664.

G. Glover et al., "An Algorithm for the Reduction of Metal Clip Artifacts in CT Reconstructions", Medical Physics, vol. 8, No. 6, Nov. 1981, pp. 799–807.

E. Klotz et al., "Algorithms for the reduction of CT Artefacts Caused by Metallic Implants", SPIE vol. 1234, (1990).

B.E. Oppenheim, "Reconstruction Tomography from Incomplete Projections", Reconstruction Tomography in Diagnostic Radiology and Nuclear Medicine, Edited by M.M. Ter–Pogossian et al. 1977, pp. 155–183.

D. Robertson et al., "Evaluation of CT Techniques for Reducing Artifacts in the Presence of Metallic Orthopedic Implants", Journal of Computer Assisted Tomography, 12(2), Mar, Apr. 1988, pp. 236–241.

A.J. Kelly et al., "Poor Reproducibility in Radiographic Grading of Femoral Cementing Technique in Total Hip Arthroplasty", The Journal of Arthroplasty, vol. 11, No. 5, 1996, pp. 525–528.

T. Hinderling et al., "Computed Tomography Reconstruction from Hollow Projections: An Application to In Vivo Evaluation of Artificial Hip Joints", Journal of Computer Assisted Tomography, 3(1), Feb. 1979, pp. 52–57.

W. Kalender et al., "Reduction of CT Artifacts Caused by Metallic Implants", Radiology, vol. 164, No. 2, Aug. 1987, pp. 576–577.

*Primary Examiner*—David Vernon Bruce
*Attorney, Agent, or Firm*—Whitham, Curtis & Whitham; Louis J. Percello

[57] ABSTRACT

A system and method reduce the noise, and hence improve the usefulness, of computer tomography (CT) images that have been corrupted by metal-induced reconstruction artifacts. Metal-induced reconstruction artifacts in CT images are reduced by restoring crucial quantitative image information. The system does not fail when applied to sparsely-sampled and/or low-resolution projection data and is clinically viable in that it is a method that can be embodied in a practical, real-world system that can be used routinely in hospitals and medical clinics, and relies only on data that are available from standard medical CT scanners.

12 Claims, 7 Drawing Sheets

SYSTEM AND METHOD FOR REDUCING RECONSTRUCTION ARTIFACTS IN COMPUTED TOMOGRAPHY IMAGES

CROSS-REFERENCE TO RELATED APPLICATION

This application is a continuation-in-part and claims the benefit of the filing date of Provisional Application Ser. No. 60/038,330 filed Feb. 26, 1997, by Alan D. Kalvin for "System and Method for Reducing Reconstruction Artifacts in Computed Tomography Images". The disclosure of Application Ser. No. 60/038,330 is incorporated herein by reference.

DESCRIPTION

BACKGROUND OF THE INVENTION

1. Field of the Invention

The present invention generally relates to the field of computer image processing of computer tomography (CT) data and, more particularly, to reducing artifacts in computed tomography images arising from the process of reconstructing the images from projections.

2. Background Description

U.S. Pat. No. 5,416,815, which is incorporated here by reference in its entirety, describes computer tomography (CT) systems and the method of image reconstruction from projections. X-ray CT images of objects containing metal are often corrupted by noise in the form of blooming and streaking artifacts that radiate from the regions of the image where the metal is present. These artifacts are referred to as "metal-induced reconstruction" artifacts, and the process of reducing their effect as "metal artifact reduction" (or MAR). Metal-induced artifacts severely limit the clinical usefulness of CT images, both for diagnostic and therapeutic purposes.

The prior art methods of MAR fall into two groups. In the first group are image processing methods which have been applied directly to the noisy CT images. See, for example, D. D. Robertson, P. J. Weiss, E. K. Fishman, D. Magid, and P. S. Walker, "Evaluation of CT techniques for reducing artifacts in the presence of metallic orthopedic implants", *Journal of Computer Assisted Tomography,* March–April 1988, 12(2), pp. 236–41; Hamid Soltanian-Zadeh, Joe P. Windham, and Jalal Soltanianzadeh, "CT Artifact Correction: An Image Processing Approach", *SPIE Medical Imaging '96,* Newport Beach, Calif., February 1996; and Heang K. Tuy, "An Algorithm to Reduce Clip Artifacts in CT Images", *SPIE Vol. 1652 Medical Imaging VI: Image Processing* (1992).

Methods which apply image processing directly, process the corrupted CT images data only. These methods do not make use of any projection data. This approach is limited by the fact that essential image information is completely erased by MAR artifacts. This information cannot be recovered solely from the corrupted images themselves. Therefore, these methods are unable to recover this information. Further, they do not directly address the problem of recovering quantitative boundary information, but rather they focus on improving the overall qualitative appearance of the images.

With the second group of methods, the projection data are processed directly (typically by filling in "missing" data), and the images reconstructed from these modified projections. See, for example, G. H. Glover and N. J. Pelc, "An algorithm for the reduction of metal clip artifacts in CT reconstructions", *Medical Physics,* 8(6), November/December 1981, pp. 799–807; T. Hinderling, P. Ruegsegger, M. Anliker, and C. Dietschi, "Computed Tomography reconstruction from hollow projections: an application to in vivo evaluation of artificial hip joints", *Journal of Computer Assisted Tomography,* February 1979, 3(1), pp. 52–57; W. A. Kalender, R. Hebel, and J. Ebersberger, "Reduction of CT artifacts caused by metallic implants", *Radiology,* August 1987, 164(2), pp. 57–7; E. Klotz, W. A. Kalender, R. Sokiranski, and D. Felsenberg, "Algorithms for the reduction of CT artifacts caused by metallic implants", *Medical Imaging IV: PACS System Design and Evaluation,* vol. 1234, Newport Beach, Calif., February 1990, pp. 642–650; R. M. Lewitt and R. H. T. Bates, "Image reconstruction from projections: IV: Projection completion methods (computational examples)", *Optik* 50, 1978, pp. 269–278; B. E. Oppenheim, "Reconstruction tomography from incomplete projections", *Reconstruction Tomography in Diagnostic and Nuclear Medicine,* Ter-Pogossian (editor), University Park Press, Baltimore, 1977, pp. 155–183; and G. Wang, D. L. Snyder, A. O'Sullivan, and M. W. Vannier, "Iterative deblurring for CT metal artifact reduction", *IEEE Trans. Medical Imaging,* October 1996, 14(5), pp. 657–664.

Methods which process projection data directly, process the projection data only. They do not make use of the CT image data. Further, a major deficiency of these methods that they work only with a very specific type of projection data; that is, projection data that (i) have been highly-sampled, and (ii) are of high resolution. The methods will fail if applied to sparsely-sampled or low-resolution projection data.

DEFINITIONS

The basic concepts described in the present invention are better understood with review of the following definitions.

PIXEL: A picture element. The basic element in a two-dimensional digital (2D) picture.

IMAGE: A rectangular 2D digital picture. Each pixel in the image is identified by a pair of integers (x,y), where x and y are the column and row locations of the pixel respectively. (We shall use the terms "slice" and "image" interchangeably in describing the present invention).

SLICE: See IMAGE.

IMAGE SEGMENTATION: The process of identifying objects of interest in an image.

SEGMENTED OBJECT: A object of interest in an image identified by the process of segmentation.

SCANNING SCENE: The region of physical space, and the physical objects within it, that are scanned by a CT scanner.

INTRINSIC SCENE OBJECT: An object that is an integral part of the scene being scanned. The CT scanner table (on which a patient lies during scanning) is an example of an intrinsic scene object.

EXTRINSIC SCENE OBJECT: An extraneous object that is deliberately placed in the scanning scene. Typically, an extraneous object is used as an aid in determining the properties of intrinsic objects. For example, an object placed in the scene for purposes of calibrating the CT scanner is an extrinsic scene object.

OBJECT CONSTRAINT: A constraint on image pixel values that is derived from information about the physical properties of the scanned objects. For example, the X-ray attenuation coefficient of a physical material can be used to restrict the pixel values of objects made from that material.

PROJECTION CONSTRAINT: A constraint on image pixel values that is derived from information about the projection data and projection geometry.

IMAGE CONSTRAINT: A general term for a constraint (either object or image constraint) on image pixel data.

IMAGE ENHANCEMENT: The process of improving the quality of a digital image by reducing image noise. In describing the present invention, we shall use the term specifically to refer to the reduction of noise caused by metal-induced reconstruction artifacts.

ENHANCED IMAGE: An image produced by application of image enhancement techniques.

IMAGE MASK: Given a digital image N, a corresponding mask image is an image with the same dimensions (i.e., the same number of rows and columns) such that each pixel value in the mask image is a code that represents a method for modifying the corresponding pixel value in the given image N.

RAY: This refers to a single X-ray beam that travels from the CT scanner X-ray tube to a detector cell on the CT scanner detector array.

RAYSUM: This refers to the basic unit of projection data collected by a CT scanner. It is the value associated with a single X-ray beam. It is a measure of the total attenuation of the beam ray as it travels from its source through the object being scanned to the CT detector array.

DERIVATIVE SET OF PROJECTION DATA: Given a set of projection data P, a derivative set of projection data D is a set of projection data derived from P that has less information content. Typical examples of sets of derivative projection data are sets produced when P is subsampled, when its resolution is reduced, or when it is otherwise filtered.

SCOUT IMAGE: A scout image is a 2D digital X-ray produced when a CT machine scans a collection of objects while the X-ray tube is held in a fixed position, and the CT table, together with the objects, is moved.

SUMMARY OF THE INVENTION

It is therefore an object of the present invention to provide a system and method to reduce the noise, and hence improve the usefulness, of computer tomography (CT) images that have been corrupted by metal-induced reconstruction artifacts.

It is a further an object to provide a system and a method for reducing metal-induced reconstruction artifacts in CT images.

According to the invention, there is provided a metal artifact reduction (MAR) system that (a) restores crucial quantitative image information; (b) is applicable to sparsely-sampled and/or low-resolution projection data; and (c) is clinically viable in that it is a method that can be embodied in a practical, real-world system that can be used routinely in hospitals and medical clinics, and relies only on data that are available from standard medical CT scanners.

More specifically, this invention consists of a technique for processing CT scans of objects (typically human medical patients) that have pieces of metal embedded within them, and an algorithm for reducing MAR artifacts in the CT images produced by the CT scanner using the technique according to the invention.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
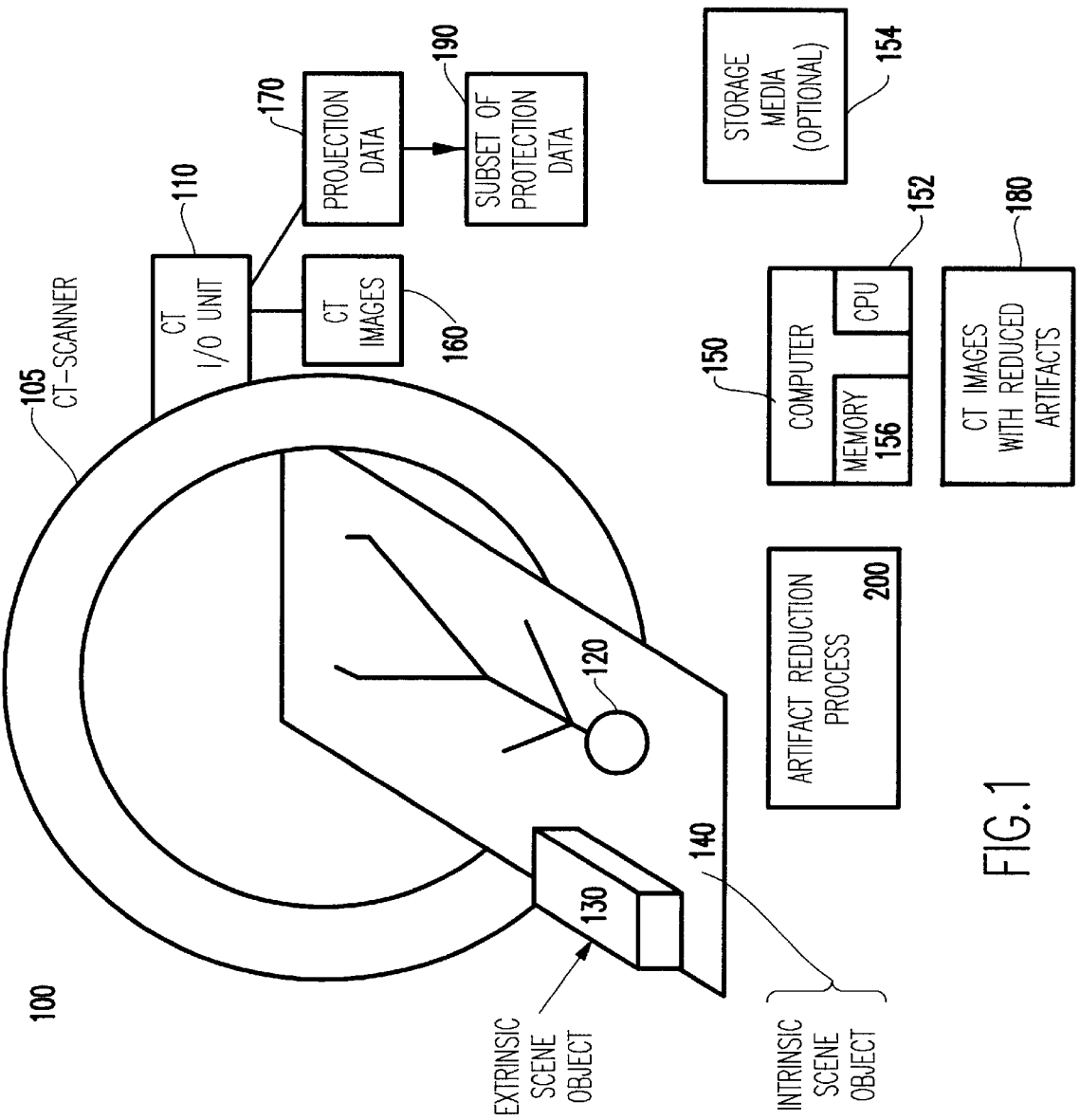
FIG. 1 is a block diagram of a computer tomography (CT) system using the present invention.

Referring now to the drawings, and more particularly to FIG. 1, there is shown one preferred embodiment of the present invention that uses image processing to reduce reconstruction artifacts in computer tomography (CT) images 160 produced by a computed tomography scanner 105. A physical object (typically a medical patient) 120 is scanned by the CT scanner 105, collecting projection data 170, from which is created a set of 2D CT images 160. This process of creating the images 160 is known as image reconstruction from projections.

The CT images 160 contain cross-sectional details of the scene that was scanned, which typically includes the patient 120, intrinsic scene objects such as the scanner table 140, and extrinsic scene objects 130. Extrinsic scene objects 130 are objects that are specifically inserted into the scene to provide additional information to the artifact reduction process. Extrinsic scene objects 130 useful for artifact-reduction generally have two common properties: (a) they show up clearly in CT images, with well-defined and distinct boundaries, and (b) their brightness values (pixel grey-level values) in artifact-free CT images are known.

The CT images 160 and some subset 190 of the related CT projection data 170 are input to a computer 150 and, optionally, stored on an external storage medium 154. The computer 150 may be, for example, an IBM RS/6000 workstation running AIX, IBM's version of the UNIX operating system, and the external storage medium 154 may be, for example, a disk storage system connected to the computer. An artifact reduction program 200 running on the computer 150 reads in the CT images 160 and projection data 190, and outputs the set of CT images with a reduced amount of artifact 180.

Figure 2:
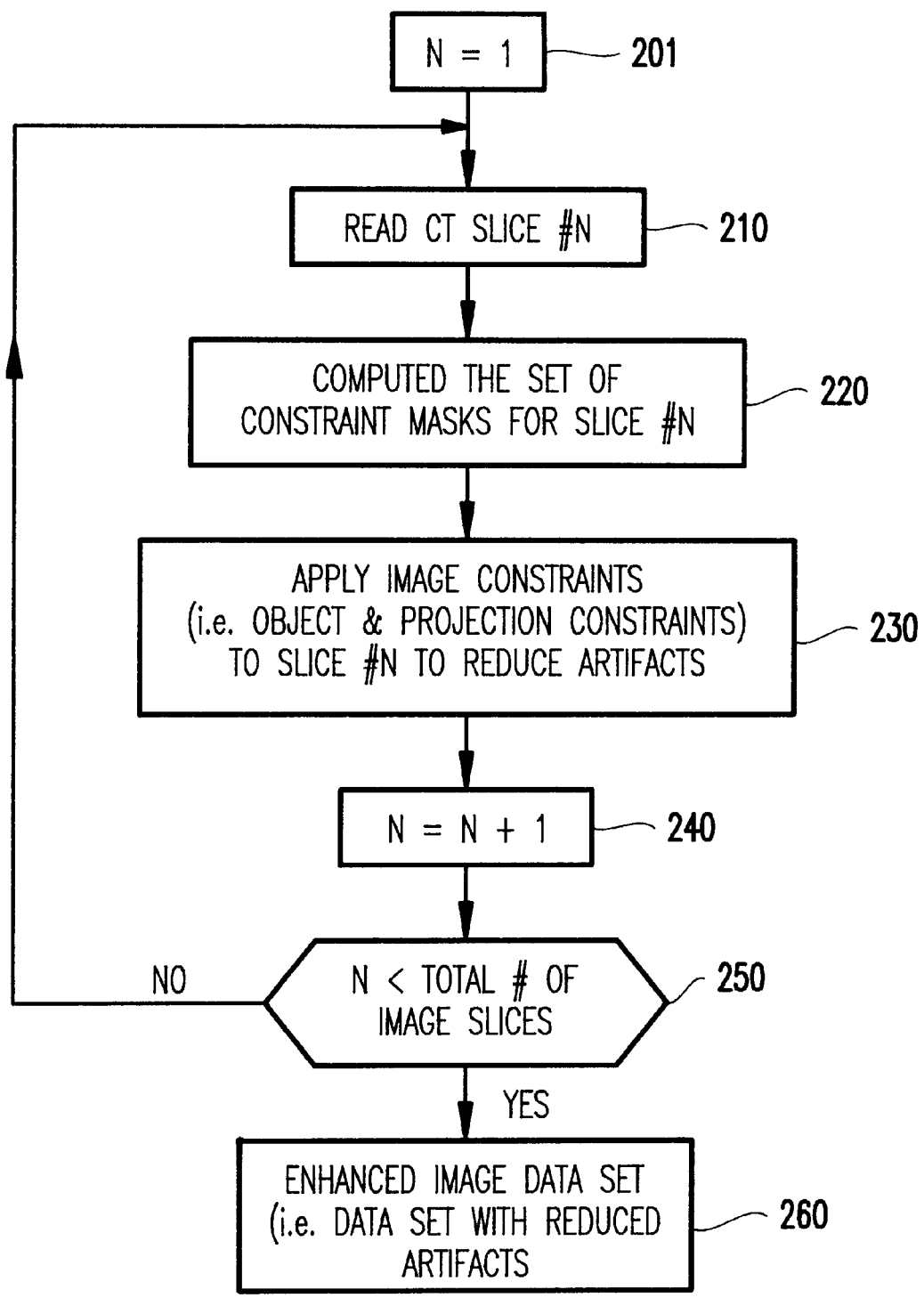
FIG. 2 is a flow chart showing the overall logic of the computer implemented process according to the invention.

FIG. 2 shows a flow chart of the artifact reduction program 200 shown in FIG. 1. Each 2D CT slice is sequentially processed as follows. When the process begins, as shown in the initialization block 201, N, the number of the slice currently being processed, is set equal to 1. In the next step, shown in function block 210, slice number N is input. In function block 220, one or more mask images are computed, based on the physical characteristics of the objects appearing in slice N. These masks are later used to apply constraints on pixel values in the slice. In the next step, shown in function block 230, image constraints (i.e. object constraints and projection constraints) are applied to slice N, to produce an enhanced version of slice N with reduced artifacts.

The steps of function blocks 210, 220 and 230 are repeated until all the slices have been enhanced. This is accomplished, following function block 230, by incrementing slice number N by 1, in function block 240. Then, a determination is made in decision block 250 as to whether N is greater than the total number of image slices. If N is less than or equal to the total number of slices, then the steps shown in function blocks 210, 220 and 230 are repeated. If N is greater than the total number of slices, then the process terminates, giving as output the complete set of enhanced 2D slices, as shown in function block 260.

Figure 3:
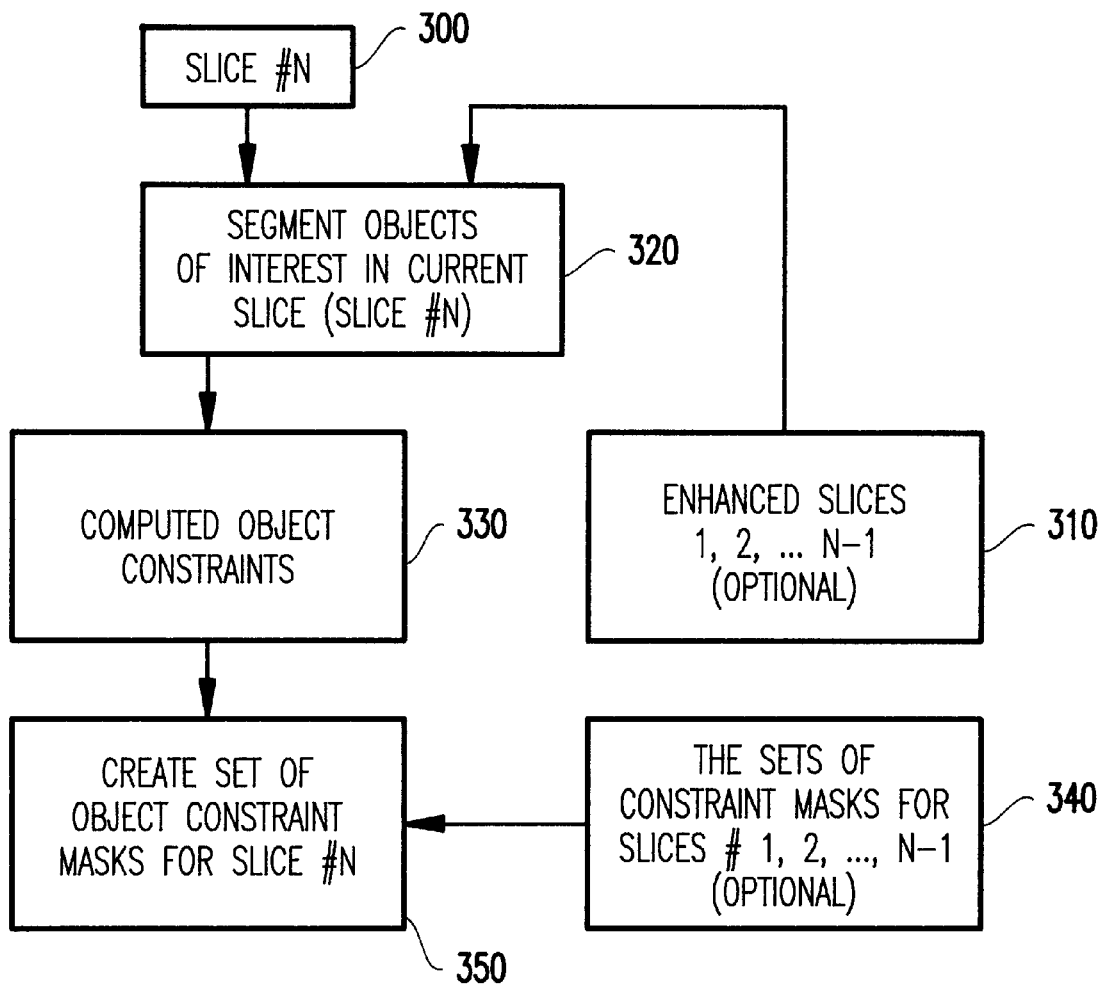
FIG. 3 is a flow chart showing the steps of computing object constraints in the process of FIG. 2.

FIG. 3 shows a flowchart of the method for computing the set of object constraint masks (function block 220 in FIG. 2). In function block 320 of FIG. 3, slice N is segmented, that is, objects of interest in slice N are identified, using known computer vision techniques (see, for example, *Computer Vision* by Ballard and Brown, Prentice Hall, 1982). All N−1 enhanced slices (numbered 1,2, . . . N−1) that have already been produced at this stage can optionally be used in the segmentation of slice N, as indicated at input block 310. From the segmentation, object constraints for slice N are computed (function block 330).

As shown in function block 350, the set of object constraint masks for slice N is then created. All currently existing sets of object constraint masks (i.e. those for slices 1,2, . . . N−1) can optionally be used in the creation of the set of masks for slice N, as indicated at input block 340. In the current preferred embodiment, M, the number of masks produced for slice N, is equal to the number of objects of interest produced by the segmentation of slice N, i.e., one mask for each object of interest.

In constructing these masks, we assume that the X-ray attenuation coefficient of each object of interest K (K=1, 2, . . . M) is known. We can do this since tables of attenuation coefficients of many materials have been published. For example, all the attenuation coefficients that are of interest to us appear in H. Hubbell and S. M. Seltzer, "Tables of X-Ray Mass Attenuation Coefficients and Mass Energy-Absorbtion Coefficients 1 keV to 20 MeV for elements Z=1 to 92 and 48 Additional Substances of Dosimetric Interest", *National Institute of Standards and Technology report NISTR* 5632, 1996. Alternatively, attenuation coefficients can be empirically evaluated.

From these attenuation coefficients, we can determine the correct grey-level (or density) value of the pixels in slice N belonging to object K, and from this information we construct the $K^{th}$ constraint mask as follows. For each slice pixel (x,y) belonging to object K, the matching mask pixel (x,y) is set equal to the correct pixel value for object K. Let us call this value $Q_R$. All other pixels in the mask are assigned a special "no-constraint" value indicating that no constraints are imposed by object K on these pixels.

Figure 4:
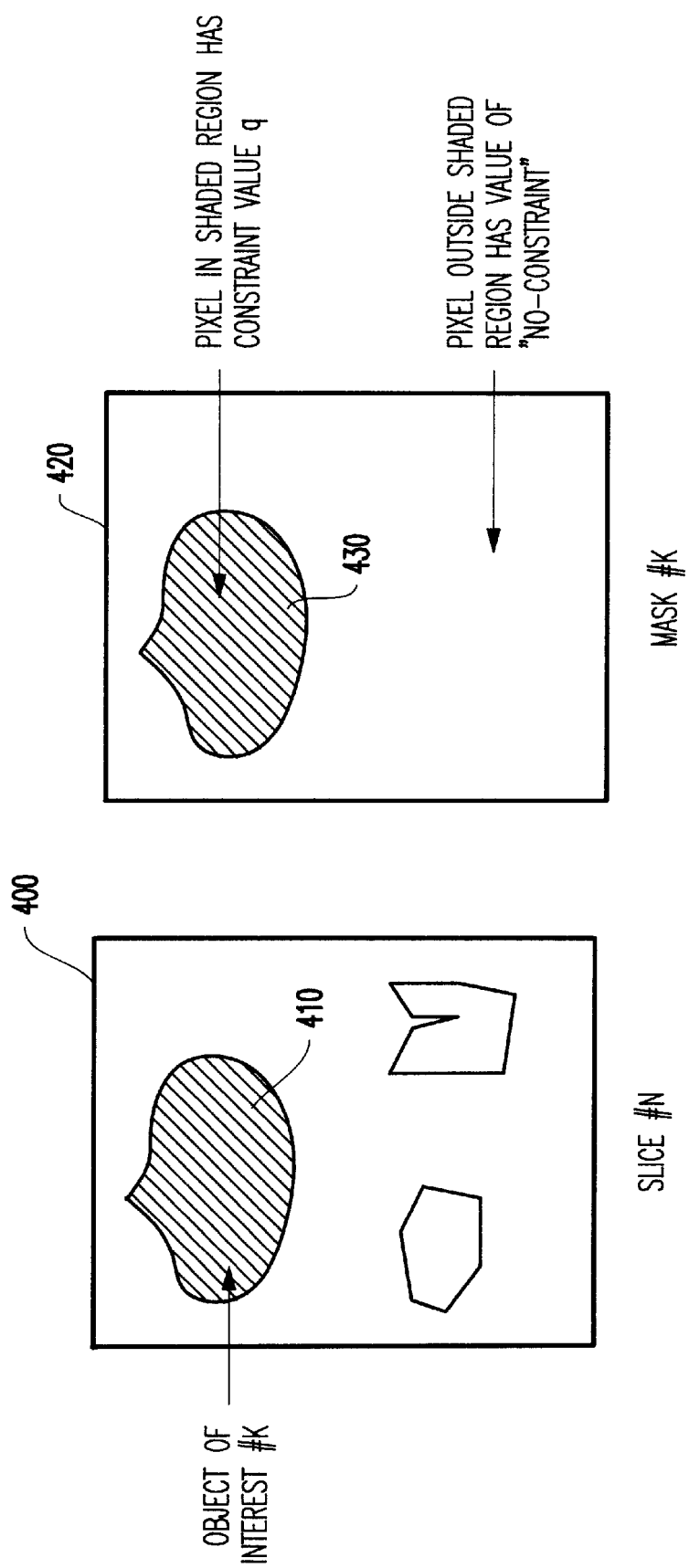
FIG. 4 illustrates how an object constraint mask is created from an object of interest in a CT slice.

FIG. 4 illustrates an example of this process. Within slice N (item 400), the $K^{th}$ object of interest 410 is shown (the shaded region). In the $K^{th}$ mask (item 420) for slice N, the value of each mask pixel (x,y) inside the matching shaded region 430 is set to $Q_K$, the correct value for slice pixel (x,y). All other pixels are set to the "no-constraint" value. (Alternative embodiments of this method can use more general constraints, for example ranges of valid values). These masks are later used to apply specific constraints during the image enhancement process (function block 540 of FIG. 5, described infra).

Figure 5:
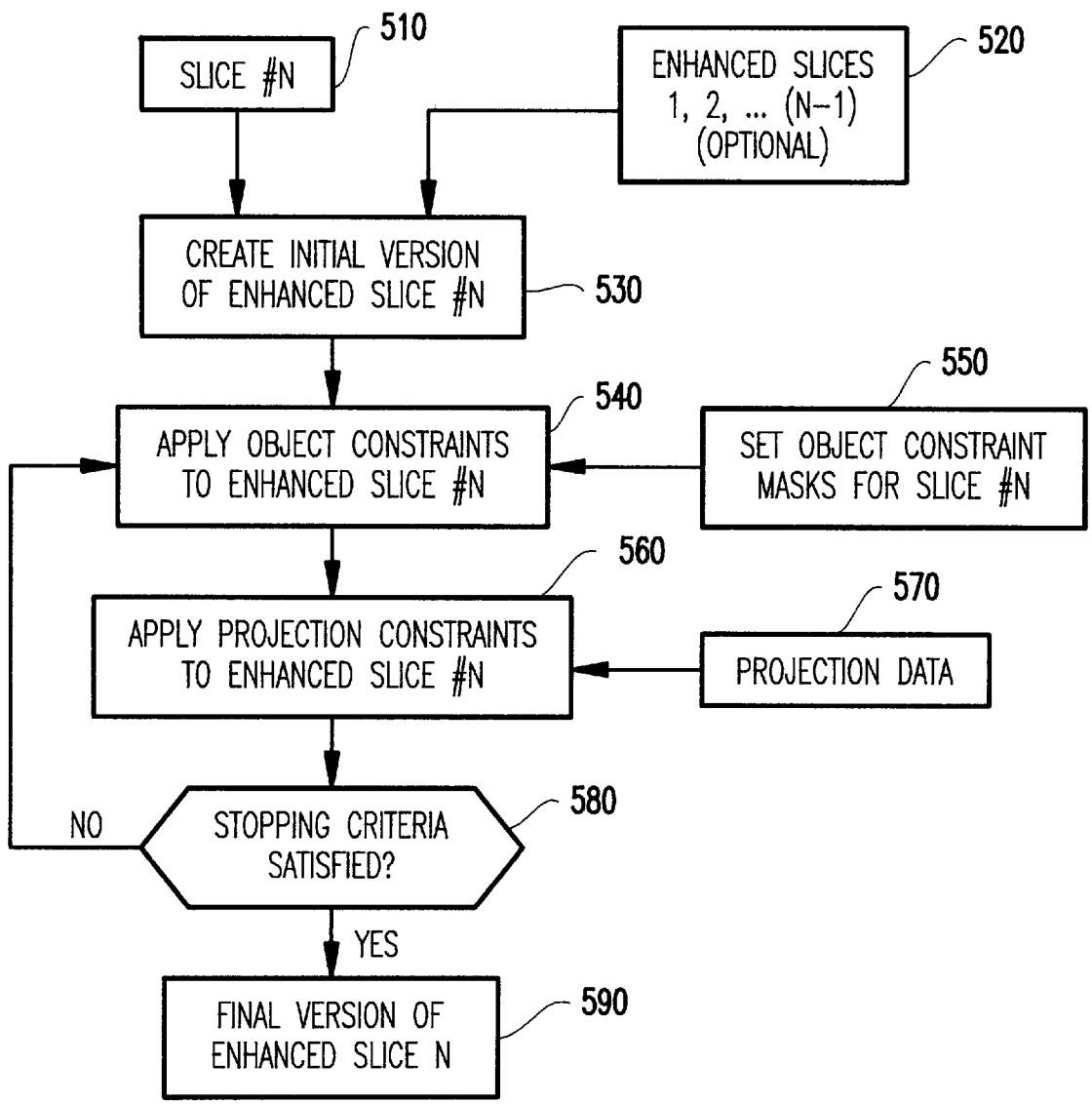
FIG. 5 is a flow chart showing the steps of the method for reducing reconstruction artifacts for a single 2D slice.

In FIG. 5, the method for reducing reconstruction artifacts is illustrated. In function block 530, an initial enhanced version of slice N, input from block 510, is created from slice N and, optionally from block 520 (i.e. from the existing N−1 enhanced slices numbered 1,2, . . . N−1). If the optional data from input block 520 are not used, the enhanced slice N is initialized by setting it equal to the original slice N (block 510). If the data from block 520 are used, initialization is achieved by combining the original slice N data (block 510) with an extrapolation of the optional data, using the fact that slices 1,2, . . . , N are a set of sequential cross-sections of a 3D object.

The step shown in function block 540 is the first step in an iterative process that is repeatedly executed until prescribed termination criteria have been met. Typically, criteria for termination are (a) the amount of change made to the enhanced slice in the previous iteration fall below a threshold, or (b) a maximum number of iterations of the loop is reached. In the step shown in function block 540, the set of constraint masks (block 550) is used to impose object constraints on slice N, which is modified accordingly. In function block 560, slice N is again modified by checking it for consistency against the projection data, shown as input from block 570, and updating it to increase the degree of consistency. (The methods applied in function blocks 540 and 560 are described in more details infra.) A test is then made in decision block 580 to determine if any of the criteria for terminating this iterative loop (as described supra) have been met. If not, another iteration is begun by looping back to function block 540. When one or more of the criteria for terminating the iterative loop have been met, the process terminates with the final version of enhanced slice N being output in block 590.

Figure 6:
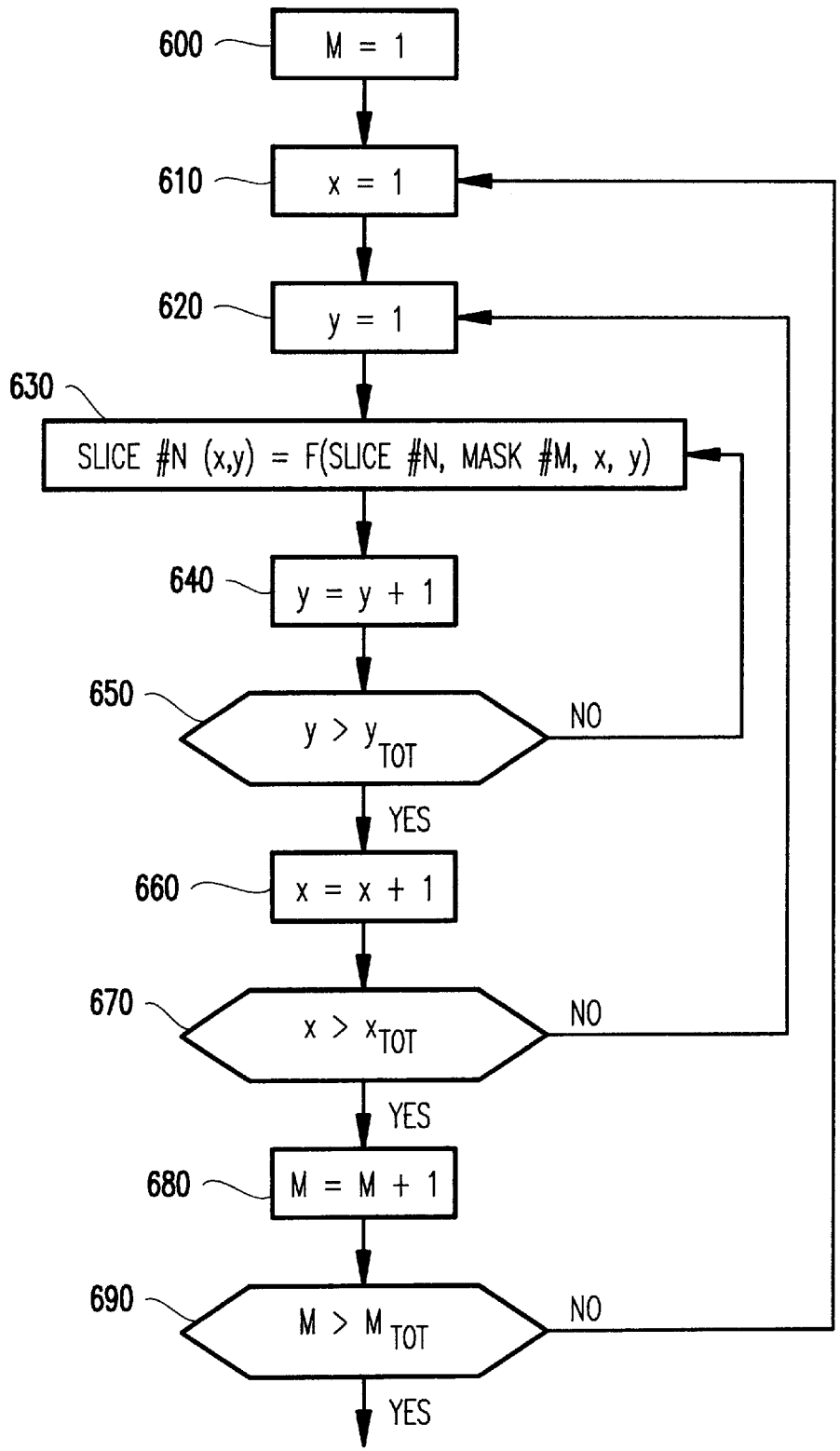
FIG. 6 is a flow chart showing the steps of applying object constraints in the process of artifact reduction.

FIG. 6 shows the steps involved in applying object constraints in the process of artifact reduction. In function block 600, M, the counter for the constraint masks for slice N is initialized to 1. In block 610, the counter for slice column is initialized to 1, and in block 620, the counter for slice row is initialized to 1. In function block 630, pixel (x,y) in slice N is modified by the function F as follows. Let v be the current value of pixel (x,y) in slice N. and let Q be the value of pixel (x,y) in mask M. If Q is the special "no-constraint" value, slice pixel (x,y) is not changed. Otherwise slice pixel (x,y) is set to Q. The y counter is incremented by 1 (block 640) and if y is not greater than $Y_{TOT}$ (the total number of rows in slice N) then the process in function blocks 630 and 640 is repeated. Similarly, the x counter is incremented and tested in blocks 660 and 670, and if x is not greater than $X_{TOT}$ (the total number of columns in slice N), the process in function blocks 620, 630, 640, 650, and 660 is repeated. In the same manner, the M counter is incremented and tested in blocks 680 and 690, and if M is not greater than $M_{TOT}$ (the total number of constraint masks for slice N), the process in function blocks 610, 620, 630, 640, 650, 660, 670, and 680 is repeated. When M finally becomes greater than $M_{TOT}$, the process shown in FIG. 6 is complete.

Figure 7:
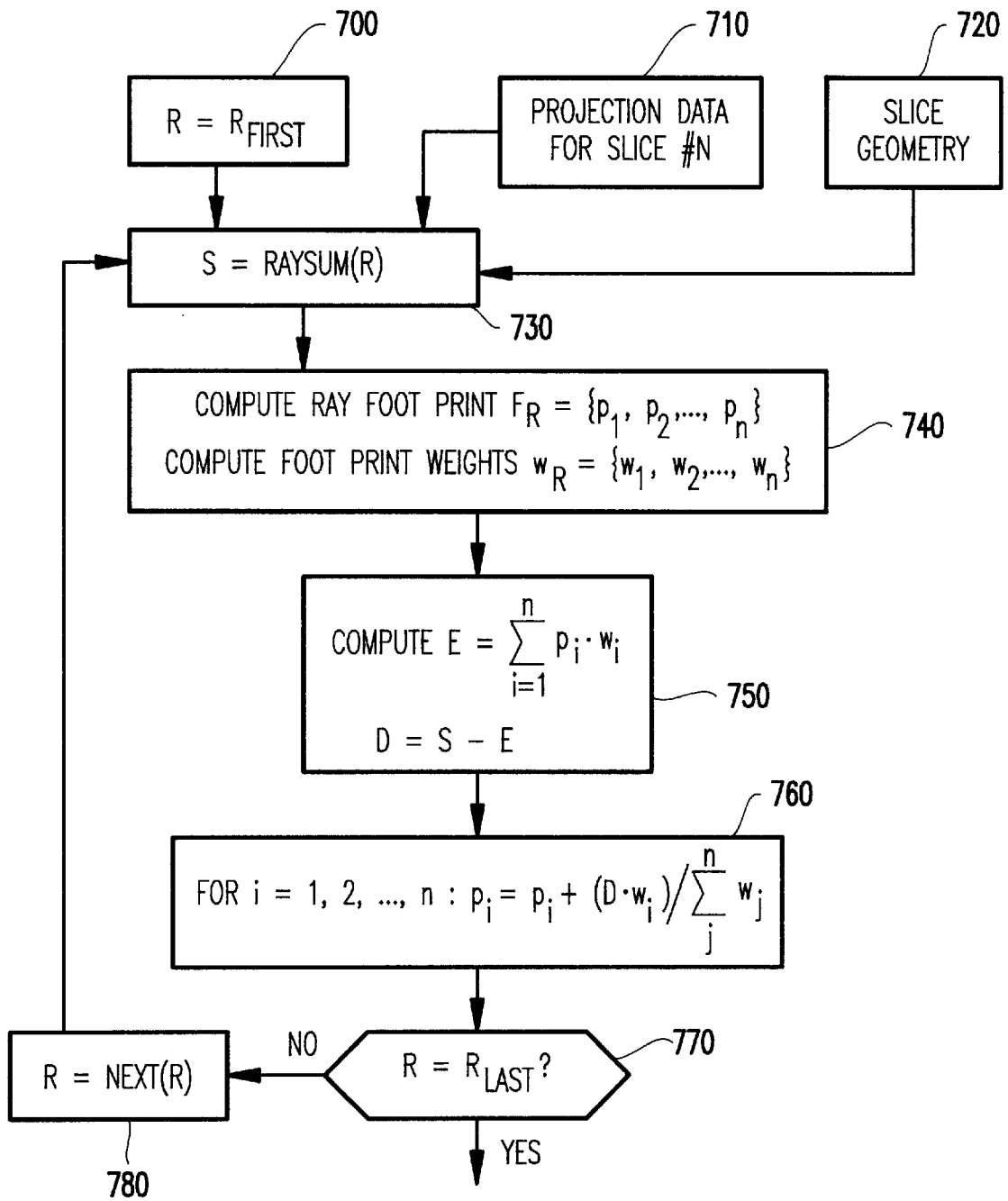
FIG. 7 is a flow chart showing the steps of applying projection constraints in the process of artifact reduction.

FIG. 7 is a flow chart showing the steps of applying projection constraints in the process of artifact reduction. This part of the invention involves iterating through all the projection rays associated with slice N. (We say that a set of rays are associated with slice N if all the rays lie in the same 2D plane in the scanning scene as slice N.) In each iteration a subset of pixels in slice N is updated according to the constraints imposed by the ray.

We make use of the following three definitions in describing the logic of the flowchart in FIG. 7. Given a ray R, the ray footprint, $F_R = \{p_1, p_2, \ldots p_n\}$, is the set of image pixels through which ray R passes. The footprint weights, $W_R = \{w_1, w_2, \ldots w_n\}$, are defined so that $w_i$ is the length of the intersection of ray R with footprint pixel $p_i$. The two sets are computed using the geometry of the projection data (i.e., the locations of the rays in the scanning scene), and the geometry of the slice, block 720 (i.e., the location in the scanning scene of the 2D cross-section depicted by slice N).

We also make use of the term raysum as defined in the "Background of the Invention" section.

In function block 700 the counter R for projection rays is set to $R_{first}$, the first ray to be used to impose projection constraints on slice N. In block 730, S is assigned the value of raysum R (obtained from the projection data in input block 710). In function block 740, the ray footprint $F_R=\{p_1, p_2, \ldots p_n\}$, and the footprint weights $W_R=\{w_1,w_2, \ldots w_n\}$, are computed. In function block 750, E, the estimated ray sum, is computed as the weighted sum of the footprint pixels. The difference D between the true ray sum S, and E is also computed. In function block 760, the projection constraints dictated by ray R are applied, by updating each footprint pixel $p_i$ (i=1,2, . . . ,n) according to the formula shown. Decision block 770 checks if $R=R_{last}$, i.e. if we have used all the rays for slice N. If the answer is no, the next ray to be used is generated (block 780), and blocks 730,740,750, and 760 are re-executed. If the answer to decision block is yes, the process shown in FIG. 7 is complete.

The function NEXT (block 780) can be any function which iterates through all the rays, generating each ray exactly once. In this preferred embodiment we use the function $$NEXT(i)=i(MOD\ R_{total})+1,$$

where $R_{total}$ is the total number of rays. It is interesting to note that the technique for applying projection constraints that is described in FIG. 7 is somewhat related to a general family of techniques known as algebraic reconstruction techniques or ART, that are used for reconstructing images from projections, that is, used for creating 2D images from projection data. (See for example, Y. Censor, "Finite Series-Expansion Reconstruction Methods", *Proceedings of the IEEE,* vol. 71, no.3, 1983, pp. 409–419). One basic, and crucial difference between the process described in FIG. 7 and the ART methods is that the former is just a single step in a multiplicity of steps that make up the present invention for image enhancement by artifact reduction. The ART methods on the other hand, are methods that solve a different problem, namely the problem of image reconstruction, and an ART method is not a single step in an larger algorithm, but constitutes the entire reconstruction algorithm itself.

Given this disclosure, alternative equivalent embodiments will become apparent to those skilled in the art. These embodiments are also within the contemplation of the invention. Thus, while the invention has been described in terms of a single preferred embodiment, those skilled in the art will recognize that the invention can be practiced with modification within the spirit and scope of the appended claims.

Having thus described our invention, what we claim as new and desire to secure by letters patent is as follows:

1. A computer implemented method of processing computed tomography (CT) images comprising:
   a) providing a multiplicity of CT images, each of said images having a value, N;
   b) setting N=1;
   c) setting a total value for $N=N_{TOT}$;
   d) computing constraints on a multiplicity of pixel values for an image, N, to be processed;
   e) applying the constraints to reduce artifacts in said image, N;
   f) adding 1 to N;
   g) determining if $N=N_{TOT}$; and
   h) repeating steps d) to g) until $N=N_{TOT}$.

2. A computer implemented method as in claim 1, wherein said step of computing constraints from said objects classified as "objects of interest" comprises the step of creating a multiplicity of mask images from a digital input of an image.

3. A computer implemented method as in claim 2, further comprising the step of using a multiplicity of enhanced images, N, and a multiplicity of masks of these enhanced images, N, for creating a set of object constraint masks of from a digital input of an image.

4. A computer implemented method as in claim 3, wherein said step of processing projection data uses a multiplicity of enhanced images, N, and a multiplicity of masks of enhanced images, N.

5. A computer implemented method as in claim 1, wherein said step of applying an artifact reduction algorithm to said image, N further comprises the steps of:
   a) creating an initial version of an enhanced image, N, from image, N;
   b) setting a stopping criteria;
   c) applying object constraints to said enhanced image, N;
   d) applying projection constraints, derived from projection data, to said enhanced image, N;
   e) determining if stopping criteria has been met; and
   f) repeating steps c) through e) until said stopping criteria has been met.

6. A computer system having one or more memories, one or more central processing units, one or more image display devices, the system further comprising:
   one or more databases of projection data, said projection data being one or more 2d data sets of values wherein each said value is an estimation of a sum of X-ray attenuation coefficients of one or more objects along one of a plurality of rays passing a collection of objects, one or more of the sums having estimation errors greater than a tolerance;
   a pixel data set of information that describes an image with noise, the data set being produced from the projection data, and the noise caused by the estimation errors; and
   a image enhancing process that iteratively changes the pixel data set to reduce the noise by computing image constraints from (a) the image data, and (b) from a derivative of the projection data, and using said constraints to modify the pixel information of one or more pixels during every iteration to create a new image.

7. A system, as in claim 6, wherein said rays emanate from a ray source and a view is a set of rays emanating from said ray source being at a fixed point in space and said derivative projection data include one or more of the views.

8. A system, as in claim 7, wherein said rays emanate from a ray source and a view is a set of rays emanating from said ray source being at a fixed point in space and said derivative projection data include one or more of said views from the fixed points in space, said views being separated by equal angular distances.

9. A system, as in claim 6, wherein the quality of the said derivative projection data can be substantially lower than the quality than the original projection data.

10. A system, as in claim 6, wherein the said derivative projection data are obtained from scout data.

11. A system, as in claim 6, wherein the said collection of objects contains one or more extrinsic objects that are inserted into the scanned scene specifically for the purpose of creating additional image constraints.

12. A system, as in claim 6, wherein one or more of the said constraints are obtained from additional CT slices of the said collection of objects.

* * * * *